(12) United States Patent
Hladuvka et al.

(10) Patent No.: US 9,406,122 B2
(45) Date of Patent: Aug. 2, 2016

(54) METHOD, APPARATUS AND SYSTEM FOR LOCALIZING A SPINE

(71) Applicants: Agfa HealthCare NV, Mortsel (BE); VRVIS ZENTRUM FÜR VIRTUAL REALITY UND VISUALISIERUNG FORSCHUNGS-GMBH, Vienna (AT); AVL LIST GMBH, Graz (AT); IMP FORSCHUNGINSTITUT FÜR MOLEKULARE PATHOLOGIE GMBH, Vienna (AT)

(72) Inventors: Jiri Hladuvka, Mortsel (BE); David Major, Mortsel (BE); Katja Bühler, Mortsel (BE)

(73) Assignees: AGFA HEALTHCARE NV, Mortsel (BE); VRVIS FORSCHUNGS GMBH, Vienna (AT); IMP FORSCHUNGINSTITUT FÜR MOLEKULARE PATHOLOGIE, Vienna (AT)

( * ) Notice: Subject to any disclaimer, the term of this patent is extended or adjusted under 35 U.S.C. 154(b) by 28 days.

(21) Appl. No.: 14/384,734

(22) PCT Filed: Mar. 14, 2013

(86) PCT No.: PCT/EP2013/055233
§ 371 (c)(1),
(2) Date: Sep. 12, 2014

(87) PCT Pub. No.: WO2013/135812
PCT Pub. Date: Sep. 19, 2013

(65) Prior Publication Data
US 2015/0036909 A1 Feb. 5, 2015

Related U.S. Application Data

(60) Provisional application No. 61/611,744, filed on Mar. 16, 2012.

(30) Foreign Application Priority Data

Mar. 15, 2012 (EP) .................................. 12159593

(51) Int. Cl.
*G06K 9/00* (2006.01)
*G06K 9/46* (2006.01)
(Continued)

(52) U.S. Cl.
CPC ................ *G06T 7/0012* (2013.01); *G06K 9/46* (2013.01); *G06T 7/0081* (2013.01); *A61B 6/505* (2013.01);
(Continued)

(58) Field of Classification Search
CPC ................ G06T 7/0012; G06T 7/0081; G06T 2207/10081; G06T 2207/20132; G06T 2207/30012; G06K 9/46; G06K 2009/055; G06K 2009/4666
USPC ......................................... 382/131, 173, 203
See application file for complete search history.

(56) References Cited

U.S. PATENT DOCUMENTS 5,803,914 A * 9/1998 Ryals .................... A61B 5/0275
128/922
7,013,032 B1 * 3/2006 Samara .................. G06F 19/321
128/922

(Continued)

FOREIGN PATENT DOCUMENTS

JP     2003250794 A * 9/2003
JP     2008-132019 A   6/2008

OTHER PUBLICATIONS

Peura et al. ("Efficiency of simple shape descriptors," 3rd International Workshop on Visual Form, May 28-30, 1997).*

(Continued)

*Primary Examiner* — Yubin Hung
(74) *Attorney, Agent, or Firm* — Keating and Bennett, LLP

(57) ABSTRACT

A method and a corresponding apparatus and system localizes a spine in an image, in particular a computed tomography (CT) image, of a human or animal body, allowing for a reduced need for computational power and/or memory on the one hand and assuring a reliable localization of the spine on the other hand. The method includes a) acquiring a plurality of slice images of at least a part of a human or animal body, and b) automatically selecting slice images and/or parts of slice images from the acquired plurality of slice images by considering at least one parameter ($\mu_z$, $v_z$, $\sigma_z$, $\Lambda_z$) characterizing a distribution of bones in the acquired slice images, wherein the selected slice images and/or parts of the slice images includes image information about the spine.

14 Claims, 4 Drawing Sheets

(51) Int. Cl.
*G06T 7/00* (2006.01)
*A61B 6/00* (2006.01)

(52) U.S. Cl.
CPC .. *G06K 2009/4666* (2013.01); *G06K 2209/055* (2013.01); *G06T 2207/10081* (2013.01); *G06T 2207/20132* (2013.01); *G06T 2207/30012* (2013.01)

(56) References Cited

U.S. PATENT DOCUMENTS

| | | | | |
|---|---|---|---|---|
| 2004/0101183 | A1* | 5/2004 | Mullick | G06T 5/50 382/131 |
| 2005/0276455 | A1 | 12/2005 | Fidrich et al. | |
| 2006/0062442 | A1* | 3/2006 | Arnaud | A61B 6/505 382/128 |
| 2007/0053562 | A1* | 3/2007 | Reinhardt | G06T 7/0083 382/128 |
| 2007/0121778 | A1* | 5/2007 | Shen | G06T 7/0042 378/4 |
| 2008/0118127 | A1* | 5/2008 | Sirohey | A61B 6/504 382/130 |
| 2008/0132784 | A1* | 6/2008 | Porat | G06T 7/0081 600/426 |
| 2009/0232378 | A1* | 9/2009 | Nakamura | G06T 7/003 382/131 |
| 2009/0274350 | A1* | 11/2009 | Pavlovskaia | G06K 9/32 382/128 |

OTHER PUBLICATIONS

Rangayyan et al. ("Method for the automatic detection and segmentation of the spinal canal in computer tomographic images," J. Electronic Imaging 15(3), 2006).*

Official Communication issued in International Patent Application No. PCT/EP2013/055233, mailed on Apr. 24, 2013.

Peng et al., "Automated Vertebra Detection and Segmentation from the Whole Spine MR Images", Proceedings of the 2005 IEEE Engineering in Medicine and Biology 27th Annual Conference, Sep. 1-4, 2005, pp. 2527-2530.

* cited by examiner

METHOD, APPARATUS AND SYSTEM FOR LOCALIZING A SPINE

CROSS-REFERENCE TO RELATED APPLICATIONS

This application is a 371 National Stage Application of PCT/EP2013/055233, filed Mar. 14, 2013. This application claims the benefit of U.S. Provisional Application No. 61/611,744, filed Mar. 16, 2012, which is incorporated by reference herein in its entirety. In addition, this application claims the benefit of European Application No. 12159593.8, filed Mar. 15, 2012, which is also incorporated by reference herein in its entirety.

BACKGROUND OF THE INVENTION

1. Field of the Invention

The present invention relates to a method and a corresponding apparatus and system for localizing a spine in an image, in particular a computed tomography (CT) image, of a human or animal body.

2. Description of the Related Art

Typically, a plurality of axial CT images of a body are acquired and subsequently stored, evaluated and/or displayed in a two- and/or three-dimensional representation. Due to the large amount of acquired image data an automatic localization of a spine in CT images is a computationally intensive and memory demanding task.

SUMMARY OF THE INVENTION

Preferred embodiments of the present invention provide a method and a corresponding apparatus and system for localizing a spine in an image, in particular a CT image, of a human or animal body allowing for a reduced need for computational power and/or memory on the one hand and assuring a reliable localization of the spine on the other hand.

Preferred embodiments of the present invention are achieved by the method and the corresponding apparatus and system described below.

A method according to a preferred embodiment of the invention comprising the following steps: acquiring a plurality of slice images of at least a part of a human or animal body and automatically selecting slice images and/or parts of the slice images from the acquired plurality of slice images by considering at least one parameter characterizing a distribution of bones in the acquired slice images, wherein the selected slice images and/or parts of the slice images comprising image information about the spine.

A corresponding method comprises automatically selecting slice images and/or parts of slice images from a plurality of slice images, the slice images having been acquired of at least a part of a human or animal body, by considering at least one parameter characterizing a distribution of bones in the acquired slice images, wherein the selected slice images and/or parts of the slice images comprising image information about the spine.

An apparatus according to a preferred embodiment of the invention comprises an image processing unit for automatically selecting slice images and/or parts of the slice images from a plurality of slice images of at least a part of a human or animal body by considering at least one parameter characterizing a distribution of bones in the acquired slice images, wherein the selected slice images and/or parts of the slice images comprising image information about the spine.

The system according to a preferred embodiment of the invention comprises an image acquisition unit, in particular a computed tomography unit, for acquiring a plurality of slice images of at least a part of a human or animal body and an image processing unit for automatically selecting slice images and/or parts of the slice images from the acquired plurality of slice images by considering at least one parameter characterizing a distribution of bones in the acquired slice images, wherein the selected slice images and/or parts of the slice images comprising image information about the spine.

Preferred embodiments of the invention are based on the approach to automatically select slice images and/or parts thereof from the acquired plurality of slice images of the body based on a slice-wise, i.e. slice-by-slice, analysis of the acquired slice images with respect to a distribution of bones in the acquired slice images. Dependent on the result of the analysis, slice images and/or parts thereof containing image information about the spine are selected and/or slice images which do not contain image information about the spine are truncated. The slice-wise analysis of the acquired slice images is based on statistics and distribution signatures of bone structures present in the slices. Preferably, the analysis of the bone profiles in the acquired slice images occurs in only one pass, i.e. the acquired slice images are analyzed slice-by-slice, e.g. beginning with slice images relating to the neck and ending with slice images relating to the legs.

By this approach, in many cases of CT images a significant portion of CT image data can be left out, e.g. slice images of the region of the legs of a body which require very often a half of the total data volume. In particular, such portions of the CT image data can be left out from the acquired slices during volume reconstruction of an according spinal image. Moreover, parts too far from the spinal canal can be masked and ignored during the search for disc and vertebra labels. As a consequence, the need for computational power and memory for a two- and/or three-dimensional image reconstruction can be reduced significantly without losing relevant image information relating to the spine so that a reliable localization of the spine in the selected images can be ensured. The latter particularly applies for a subsequent estimation of what vertebral discs are likely to be found in particular selected slice images.

The term "selecting slice images" in the meaning of the present invention does not only relate to selecting slice images but also to refusing slice images or masking a part thereof. Accordingly, "selected slice images" in the meaning of the present invention are slice images and/or parts thereof which were selected or which were not truncated or masked, respectively.

A "distribution of bones" in a slice image in the meaning of the present invention relates to a distribution or spread of intensity values or pixels relating to bones in a slice image. Preferably, the intensity values of the slice images are given in and/or transformed to a Hounsfield scale in Hounsfield units (HU), wherein the intensity values are spread over an interval $g \in [350; 1050]$ HU so that bones can therefore roughly be segmented by an interval threshold.

A "parameter characterizing a distribution of bones" in the meaning of the present invention relates to one or more properties of the distribution of bone structures within a slice image. Preferably, the parameter can be derived from the bone distribution and/or it can be, e.g., a mean value or a median value of the intensity values or pixels relating to bones, a spread, a width, a variance or a standard deviation of the bone distribution. As will be set forth below in detail, there are a number of further preferred parameters which characterize the distribution of bones.

Preferably, the spine has a longitudinal axis and the image plane of respective slice images is substantially perpendicular to the longitudinal axis of the spine. Therefore, slice images in the meaning of the invention are called axial images.

In a preferred embodiment of the invention the at least one parameter relates to a center of gravity of pixels relating to bones in a slice image. The center of gravity of pixels relating to bones in a slice image relates to an average location of a distribution of the pixels relating to the bones within the slice image. Assuming that a slice image only contains a cross-sectional image of a more or less symmetric vertebra of the spine, the center of gravity will be located approximately in the center of the cross-sectional image of the vertebra. By this, a simple and reliable localization of the spine within a slice image and an according selection of the slice image is achieved.

In the meaning of the present invention, the term "pixel" denotes a smallest element of an image, in particular a picture element of a slice image. Preferably, each of the pixels exhibits an intensity value of 0 or 1 after the interval threshold has been applied.

In the case that additional bones, e.g. pelvis or ribs, contribute to the bone distribution in a slice image of a spine, the center of gravity of the intensity values will shift away from the center region of the vertebra. In order to account for this, it is preferred that the at least one parameter represents a refined center of gravity of pixels relating to bones being located within a refinement window in a slice image, wherein the refinement window is spanned around an original center of gravity of pixels relating to bones in a slice image. In this embodiment, an original center of gravity of intensity values in a slice image is determined as stated above. Next, an asymmetric refinement window is superimposed onto the slice image, wherein the dimensions and position of the refinement window is, preferably automatically, chosen so that the cross-sectional image of the spine or a part thereof is located within the refinement window, whereas additional bones, e.g. pelvis or ribs, are located outside the refinement window. In a further step, the refined center of gravity is derived only by considering pixels relating to bones which are located inside the refinement window. That way, a reliable and fast localization of a spine can also be achieved in slice images containing image information on additional bones.

In a particularly preferred embodiment, slice images are selected by considering a difference between the original center of gravity and the refined center of gravity. Because the refined center of gravity will deviate from the original center of gravity in cases where in addition to the spine additional bones are imaged, the difference between the original center of gravity and the refined center of gravity correlates with the reliability of a seed, which is a point inside or close to a vertebral body, in particular an initialization point for a subsequent segmentation algorithm. As a consequence, the smaller the difference the more reliably the seed aligns with the spine.

In another preferred embodiment of the invention the at least one parameter represents a standard deviation of pixels relating to bones in a slice image. The standard deviation of the intensity values characterizes a variation or "dispersion" from an average intensity value in an intensity value distribution of bones within a slice image. E.g., a low standard deviation indicates that the data points tend to be very close to the mean value, whereas a high standard deviation indicates that the data points are spread out over a large range of values. Thus, the standard deviation represents an easily obtainable and reliable parameter for determining whether a slice image mainly contains image information of a spine or it contains also information on additional bones.

In the meaning of the present invention, the term "standard deviation of pixels relating to bones" refers to a spatial deviation of bone pixels from the centroid of the thresholded slice images.

It is particularly preferred, that slice images are selected in which the standard deviation is within a pre-defined range. It has been found that axial slice images in the lumbar part of a body exhibit a standard deviation which is mainly characterized by the size of the vertebra of typically 25 mm imaged in the slice. Therefore, slice images exhibiting a standard deviation of the pixels relating to the bones in the region of approximately 20 to 40 mm, in particular 25 to 35 mm, in particular 25 to 30 mm, can be assigned to slice images of the lumbar column of the body, whereas slice images exhibiting a standard deviation larger than 40 mm indicate the presence of non-vertebra bones, e.g. ribs or pelvis.

In a further preferred embodiment the at least one parameter relates to at least one histogram of pixels relating to bones in a slice image in a left-to-right direction (LR) and/or an anterior-posterior direction (AP). A histogram in the meaning of the invention relates to a representation of a probability distribution of the intensity values which were classified into a pre-defined number of disjoined categories, so-called bins. Thus, a histogram represents probability values for respective pixels relating to bones in a slice image within a pre-defined bin, i.e. an intensity category. Preferably, the at least one histogram is located, in particular centered, at a refined center of gravity. Alternatively or additionally it is also preferred that the at least one parameter relates to at least one 4-bin histogram. By considering at least one histogram in LR and/or AP direction, a reliable identification of slice images relating to images containing legs of the body can be achieved. As leg slice images do not contain information on the spine, they can be truncated subsequently. By this, a reliable selection, i.e. truncation, of slice images and a subsequent localization of the spine in the selected, i.e. not truncated, slice images is possible.

Moreover, it is preferred that slice images showing a histogram of the pixels relating to bones dominant in the left-to-right direction are truncated. Alternatively or additionally it is also preferred that slice images showing a histogram of the pixels relating to bones with substantially no contribution in the anterior-posterior direction are truncated. By these provisions a very reliable identification of slice images containing images from the legs of a body and their subsequent truncation can be achieved.

As already exemplarily explained above, it is one preferred aspect of the invention that the selection step in which slice images are selected also comprises truncating slice images which are assigned to a further part, in particular to the legs, of the body. Alternatively or additionally, it is also preferred that the selection step comprises truncating image information from slice images, in particular from the selected slice images, wherein the truncated image information is assigned to a region beyond a volume around the spine. Preferably, the volume around the spine is given by a rectangular prism. By this, the total data volume is reduced considerably so that computational power and memory requirements for displaying and/or analyzing the selected slice images can be reduced significantly without adversely effecting the localization of the spine in the selected slice images.

As already mentioned above, the selected slice images can be displayed and/or analyzed for diagnostic purposes. Preferably, the selected slice images are displayed in a volume reconstruction of the slice images. Alternatively or additionally, the selected slice images are analyzed for diagnostic purposes by searching for at least a part of the spine, in particular for a spinal disc and/or vertebra.

In a preferred embodiment of the invention the acquired slice images, in particular the selected slice images, are analyzed by correlating the standard deviation of pixels relating to bones in a slice image with a model of a full-body scan. Preferably, the considered model of a full-body scan depends on parameters relating to the particular body that was scanned, e.g. sex and/or body height and/or body weight. That is, the considered model of a full-body scan contains predefined standard deviation values of a bone distribution which is typical for the respective type of body, e.g. male, range of body height 160 to 180 cm, range of body weight 60 to 80 kg. Of course, also other types of models of a full-body scan can be considered. Preferably, when correlating the standard deviation of pixels relating to bones in a slice image with a model of a full-body scan, at least one correlation parameter is determined for a plurality of the slice images and subsequently analyzed. In this way, a reliable localization of a spine or parts thereof in a plurality of slice images is possible without intervention by operation personnel in many cases and without special markers in or on the body.

Further advantages, features and examples of the present invention will be apparent from the following description of following figures.

DETAILED DESCRIPTION OF THE PREFERRED EMBODIMENTS

Figure 1:
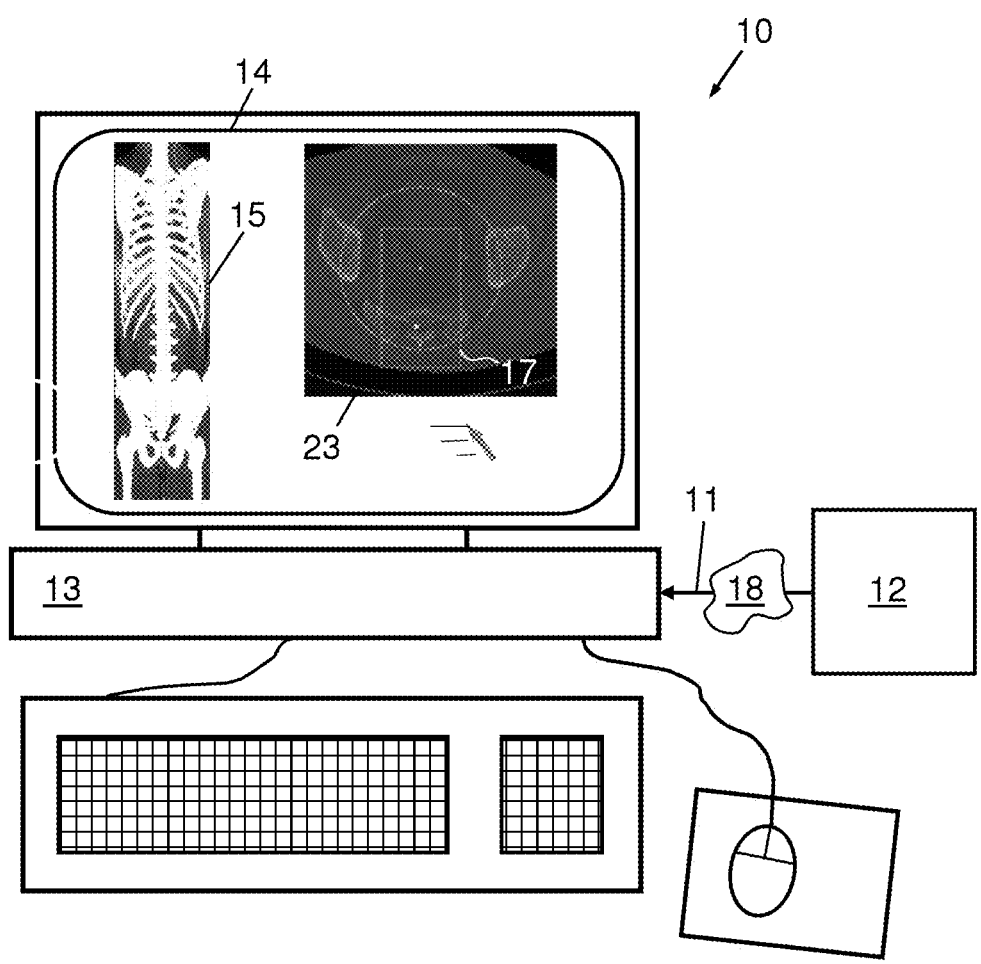
FIG. 1 shows an example of an apparatus according to a preferred embodiment of the invention.

FIG. 1 shows an example of an apparatus 10 according to a preferred embodiment of the invention. A medical data set 11 comprising a plurality of images, in particular axial slice images, of a body is acquired by a medical imaging apparatus 12, in particular a CT apparatus, and is fed to a control unit 13, preferably a computer, which is configured to control and/or to execute steps of the method according to preferred embodiments of the invention. The image data of the plurality of images can be directly fed to the control unit 13. Alternatively or additionally, image data can also be transferred via a data network 18 to which both the imaging apparatus 12 and the control unit 13 are, at least temporarily, connected.

The apparatus 10 preferably comprises a display 14, e.g. a TFT screen, for displaying slice views and/or volumetric views of the medical data set. In the example given in FIG. 1, a coronal CT slice image 15 of a human body and a corresponding axial CT slice image 23 of the lumbar part of the body are displayed. Preferably, the control unit 13 is also configured to generate a volume reconstruction of slice images 15, 23, in particular of automatically selected axial slice images, on the display 14.

As already mentioned above, preferred embodiments of the present invention are based on the approach that before localizing or labeling spines in CT scans a significant amount of the data is cropped so that both time and memory performance of an according method and apparatus for spine localization or labeling can be enhanced significantly. In the following, a one-pass, slice-wise method to figure out what parts of CT data can be left out from a DICOM-to-volume reconstruction and to estimate what vertebral discs are likely to be found in what slices is described exemplarily.

According to a preferred embodiment of the invention, in many cases a significant portion of the CT data can be truncated. For example, leg slices (often a half of the data) can be left out already during volume reconstruction from the DICOM slices. Moreover, parts too far from the spinal canal can be masked and ignored during the search for disc and vertebra labels. To cope with the above, a preferred embodiment of the present invention provides a one-pass, slice-wise method based on statistics and distribution signatures of bones structures present in particular slices. Preferred embodiments of the invention also provide an according apparatus and system for carrying out the mentioned method.

Preferably, the input scan and the accompanying DICOM fields fulfill at least one, preferably all, of the following requirements:

CT with Hounsfield scale, wherein it is assumed that there is a RAW data to Hounsfield intensity transformation, axial CT slices, so that a slice-wise iteration can be performed, head-first face-up (supine) orientation of the patient, or a transformation to yield such an orientation, and pixel/voxel size given in millimeters, or a corresponding scaling information from DICOM.

The term "RAW data" relates to original vendor's slices with intensities in CT values. This is the data produced and stored by a CT scanner where the range of pixel intensities are preset by the vendor of the CT scanner and may differ per scanning protocol.

It is further preferred that the intensity values are spread over an interval $g \in [350; 1050]$ in Hounsfield units (HU) so that bones can therefore roughly be segmented by an interval threshold. Accordingly, for a set $B_z$ of 3D positions p within a slice z where a bone is detected it applies:

$$B_z = \{(p^x, p^y, p^z) | p^z = z \wedge 350 < g(p) < 1050\} \quad (1)$$

where $p^x$, $p^y$ and $p^z$ are world coordinates in millimeters. Therefore, the set $B_z$ represents a set of bone pixels in the slices exhibiting intensity values of 1 after thresholding.

Centroid and Deviation Vector

The simplest features are based on a centroid, i.e. a center of gravity $\mu_z$, of $B_z$ $$\mu_z = \frac{1}{|B_z|} \sum_{p \in B_z} p = (\mu_z^x, \mu_z^y, z) \quad (2)$$

and the length $\|\sigma_z\|$ of a standard deviation vector $\sigma_z$ $$\sigma_z = \sqrt{\frac{1}{|B_z| - 1} \sum_{p \in B_z} (p - \mu_z)^2} = (\sigma_z^x, \sigma_z^y, 0) \quad (3)$$

$$\|\sigma_z\| = \sqrt{(\sigma_z^x)^2 + (\sigma_z^y)^2} \quad (4)$$

It has been found that centers of gravity $\mu_z$ correlate with a spine reliably in lumbar slices where pelvis, ribs, or head do not contribute to the centroid. The lumbar part can be characterized by deviation lengths $\|\sigma\|$ related to size of vertebra of approximately 25 mm seen in an axial slice. Therefore, values of $\|\sigma_z\|$ larger than approximately 40 mm indicate the presence of non-vertebra bones.

Asymmetric Mean Shift

While reliable in the lumbar area of the body, the centroids may drift remarkably from spine if the pelvis or ribs contribute by its pixels. This is illustrated by means of three examples of slice images 20, 21 and 22 shown in FIG. 2.

In the first slice image 20 the intensity values of lumbar bones 1 significantly contribute to the calculation of the center of gravity $\mu_z$, which is therefore considerably shifted away from a centroid of the vertebra 2. The radius of the circle 24 indicated in the slice image 20 corresponds to the length $\|\sigma_z\|$ of the standard deviation vector $\sigma_z$ of the intensity value distribution in the first slice image 20.

As obvious from the second and third slice image 21 and 22 a shift of the calculated center of gravity $\mu_z$ away from the centroid of the respective spine 2 is still present, albeit considerably smaller than in the first slice image 20 due to a smaller contribution of the intensity values of surrounding bones 3 or 4, to the total intensity value distribution in the slice image 21 and 22, respectively. Moreover, the small radius of the circle 24 corresponding to the length $\|\sigma_z\|$ of the standard deviation vector $\sigma_z$ in the second slice image 21 indicates that there are less bones 3 distributed far around the spine 2 than in the first or the third slice image 20 or 22, respectively.

In order to avoid the above-mentioned shift of the center of gravity $\mu_z$, the centroids within a rectangular window 17 (see FIG. 2) which is asymmetrically spanned around an original center of gravity $\mu_z$ are refined as follows:

$$W_z = \{p \in B_z | -40 \leq p^x - p_z^x \leq 40 - 40 \leq p^y - p_z^y \leq 100\} \quad (5)$$

$$\text{or } W_z = \{p \in B_z | -40 \leq p^x - p_z^x \leq 40, -100 \leq p^y - p_z^y \leq 400\} \quad (6)$$

where the correct variant of $W_z$ determined by the orientation of the patient inside the CT scanner: face-up (according to equation (5) above) and face-down (according to equation (6) above).

The original center of gravity $\mu_z$ is refined to a refined center of gravity $v_z$ of bone pixels in this window 17:

$$v_z = \frac{1}{|W_z|} \sum_{p \in W_z} p \quad (7)$$

The difference between the original $\mu_z$ and the refined $v_z$ centroids $\|\mu_z - v_z\|$ correlates with the reliability of the seed, i.e. the smaller the difference $\|\mu_z - v_z\|$, the more reliably the seed aligns with the spine.

Figure 2:
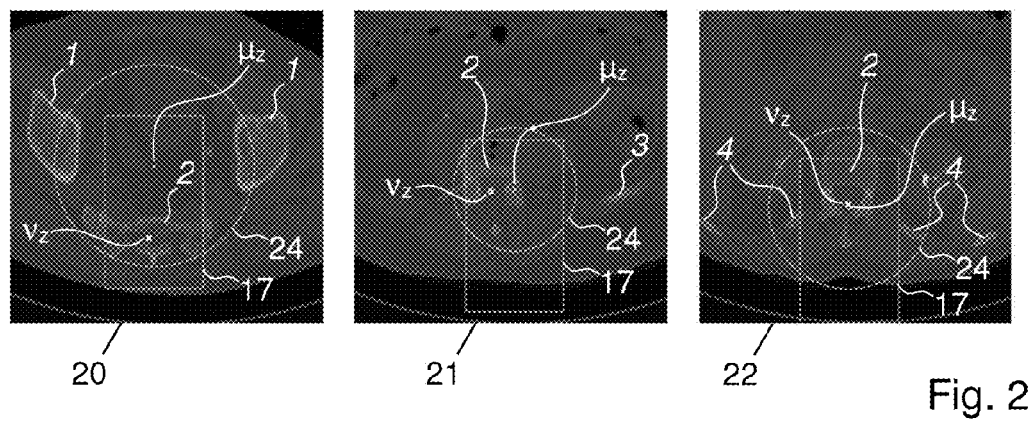
FIG. 2 shows three examples of slice images in which a center of gravity, a refinement window and a refined center of gravity is indicated respectively.

In each of the slice images 20, 21, and 22 of FIG. 2 a 80×40 mm refinement window 17 and a refined center of gravity $v_z$ is shown. Accordingly, the refined center of gravity $v_z$ is now in the region of the central axis of the respective part, e.g. a vertebra, of the spine 2.

Shape Histograms: AP Versus LR Distribution

According to a preferred embodiment of the method according to the invention leg slice images are identified by means of bone distributions being dominant in the left-to-right (LR) direction and having a zero contribution in the anterior-posterior (AP) direction.

Figure 3:
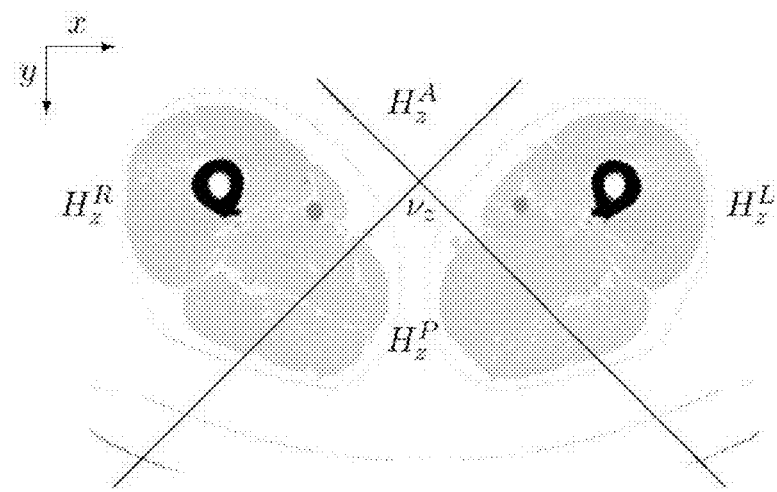
FIG. 3 shows an example of a 4-bin histogram together with a slice image.

This is illustrated by means of FIG. 3 which shows a negative of an axial CT slice showing legs and a CT table, on which the patient was lying during CT image acquisition, together with right, left, ante and poste histogram bins centered at the refined center of gravity $v_z$. In cases where the deviation vector $\sigma_z$ fails to discriminate leg slices, 4-bin histograms located in the refined centers are constructed. Putting $\delta = p - v_z$ the following four quantities are defined:

$$H_z^A = |\{p \in B_z | \delta^y < -|\delta^x| \leq 0\}| \quad (8)$$

$$H_z^P = |\{p \in B_z | \delta^y > |\delta^x| \geq 0\}| \quad (9)$$

$$H_z^R = |\{p \in B_z | \delta^x < -|\delta^y| < 0\}| \quad (10)$$

$$H_z^L = |\{p \in B_z | \delta^x > |\delta^y| > 0\}| \quad (11)$$

If the patient was positioned face-down (instead of face-up), $H_z^A$ and $H_z^P$ are to be swapped.

By the AP/LR histograms the leg detection is reformulated as a search for slices, where ante-poste bone contributions vanish:

$$\Lambda_z = \frac{H_z^A}{H_z^L + H_z^R} \approx 0 \quad (12)$$

In this preferred reformulation, the posterior voxels, i.e. volume image pixels, $H_z^P$ have been excluded from equation (12) in order to ignore an eventual contribution of a CT table.

Bone Profiles

According to the steps outlined above, it is preferred that for each of the slice images two scalars $\sigma_z$ and $\Lambda_z$, i.e. the standard deviation $\sigma_z$ and a value $\Lambda_z$ representative of contributions of bones in ante-poste direction, are derived. With these two features the slices can be easily identified in a context. Preferably, in order to identify and/or classify the slice images even more reliably, a longer feature vector containing more than two scalars can be established.

Figure 4:
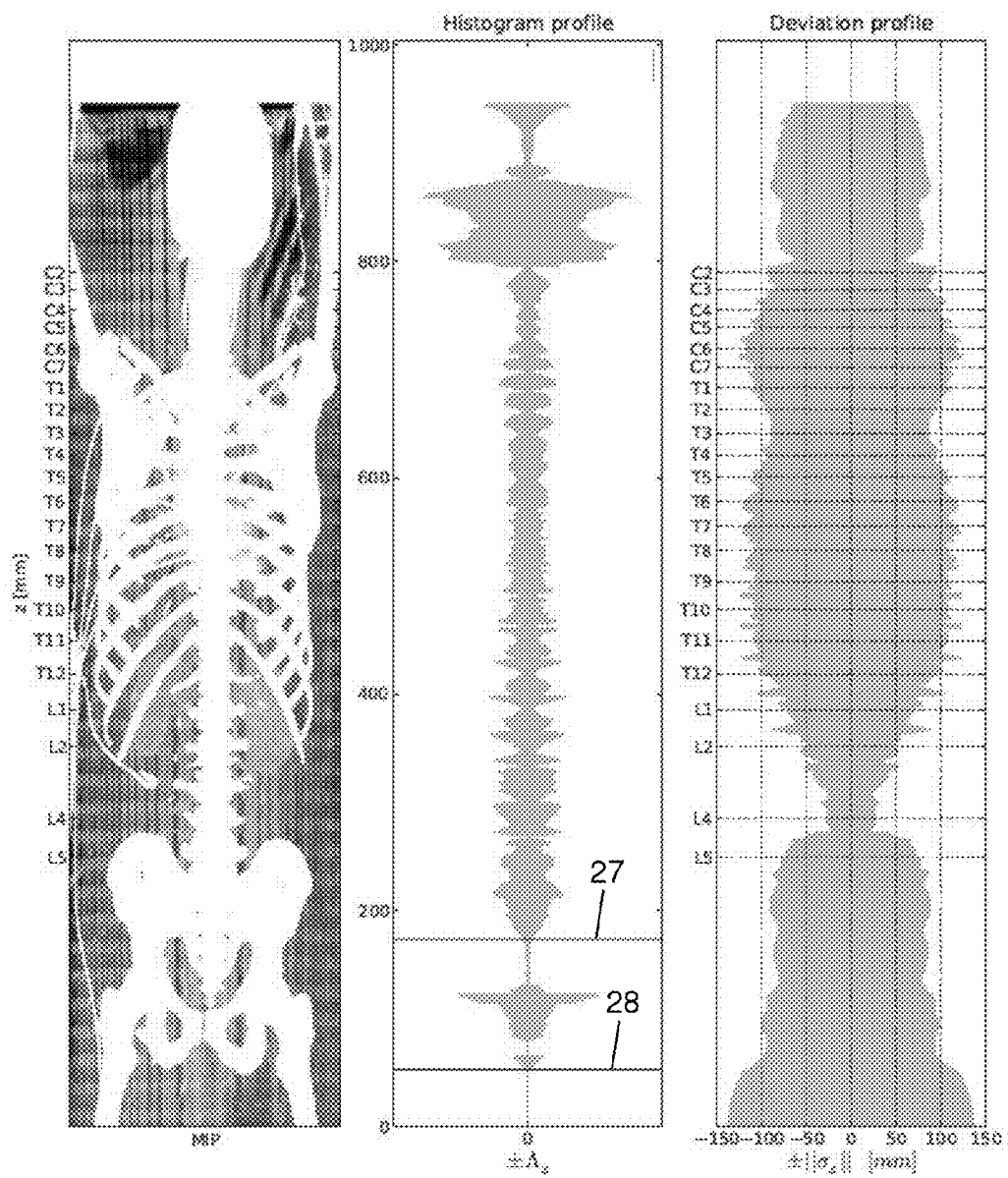
FIG. 4 shows an example of a histogram and a standard deviation profile derived from axial CT slice images together with a respective coronal projection.

FIG. 4 shows an example of a coronal projection (left) together with a respective histogram profile $\Lambda_z$ (middle) and a standard deviation profile $\sigma_z$ (right) derived from axial CT slice images. The two-dimensional plot of the parameters $\sigma_z$ and $\Lambda_z$ along the z-axis yields what is also referred to as "bone profiles". In the following it will be shown how the above-mentioned parameters contribute to localize the spine according to preferred embodiments of the invention.

Cropping the Legs: At Ischium or Near to it

Usually, slice images comprising image information of the legs and/or of a lower part of the pelvis are unnecessary to deal with when labeling the spine. In order to identify and crop respective slice images from the CT scan, the $\Lambda_z$ profile is examined automatically by the control unit 13 (see FIG. 1) from top to down for a sufficiently long chain of zeros (cf. equation 12 above). Preferably, ischium or a slab between ischium and sacrum is identified by means of a $\Lambda_z$ profile having a "zero chain" with a length of at least 20 mm. This is indicated by lines 27 and 28 in FIG. 4. Therefore, it is preferred to discard slice images below the line 28 and it is even more preferred to discard slice images below the line 27.

XY-Cropping: Near Vertebrae

After the legs have been cropped the search space far from the spine is further pruned. For upright spines, lumbar slices having a standard deviation $\|\sigma_z\|$ of pixels relating to bones of approximately 25 ($\|\sigma_z\| \approx 25$) yield a good seed to set up a cropping box for the entire volume of the selected slice images. This approach leads to an additional significant reduction of the total data volume on the one hand and ensures a reliable identification of all relevant parts of the selected slice images on the other hand, in particular for cases in which no scoliosis or oblique spines are subject to an examination.

In cases of scolioses, oblique spines and scans without lumbar part it is preferred to consider at least a part, preferably approximately 40%, of the most reliable centers of gravity for which the original center of gravity $\mu_z$ and the refined center of gravity $v_z$ overlap at least partially (so that $\mu_z \approx v_z$) in order to generate a cropping box around the spine. Preferably, rectangles of a size of approximately 90×120 mm are centered at respective refined centers of gravity $v_z$ and spanned around the spine. A resulting cropping box is preferably achieved by an x-y hull of this extrusion. By these, an undesired cropping of data in the y-direction related to the neck of the body can be reliably avoided in cases of scolioses, oblique spines and scans without lumbar part.

Disc Labels: Approximation

In order to obtain an estimate of what portion of the human body was scanned, it is preferred to correlate the deviation profile $\sigma_z$ of a particular scan, i.e. a plurality of acquired and/or selected slice images, with a ground-truth labeled model of a full-body scan. Moreover, it is preferred that it is, at least approximately, determined what labels are to be expected in particular slice images.

Figure 5:
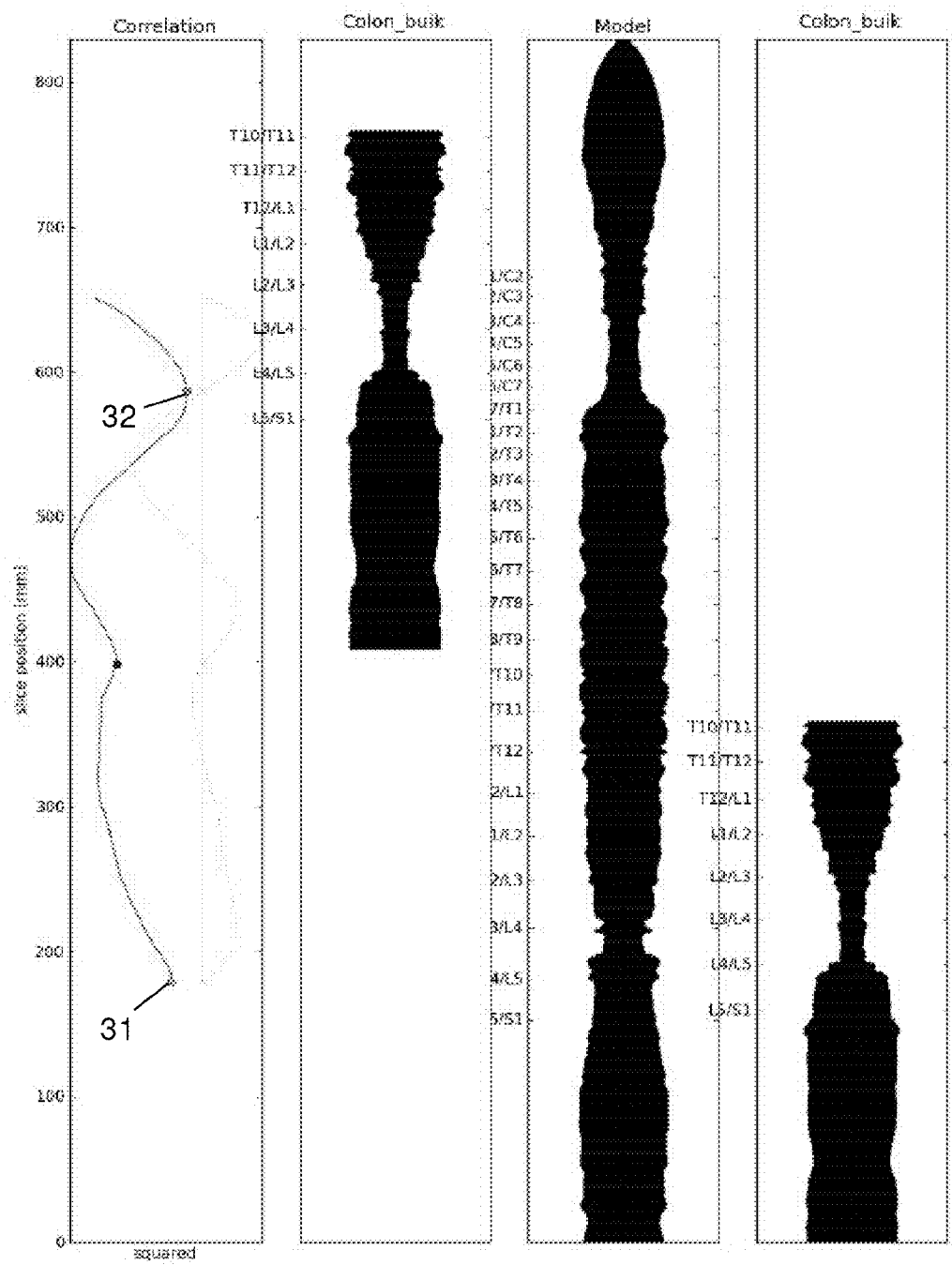
FIG. 5 shows an example of a correlation between a plurality of selected axial CT slice images with a model of a full-body axial CT scan.

FIG. 5 shows an example of a correlation between a plurality of selected axial CT slice images (denoted "Colon_buik") with a model (denoted "Model") of a full-body axial CT scan. A number of slice positions along the z axis of the model are labeled with respective vertebra labels, e.g. "C2", "T1", "L1" and "S1" and/or respective spinal disc labels, e.g. "C1/C2", "T1/T2", "L1/L2" and "L5/S1".

As obvious from FIG. 5, the respective correlation factor curve (left part of FIG. 5) shows two maximum points 31 and 32 indicating a high correlation between the two shown axial slice images "Colon_buik" with the model. As obvious from a comparison of the vertebra and/or spinal disc labels of the model and the "Colon_buik" slice images shown on the right part of the FIG. 5, in the correlation corresponding to the maximum point 31 the selected axial CT slice images fit very well to the respective part of the model. By this, a reliable localization of vertebrae and/or spinal discs in an axial CT scan can be achieved.

Further Preferred Embodiments of the Invention

Similar to leg slices, classifiers for knees can also be derived from the Λ profiles. Localization of other organs (e.g., neck, heart, kidney) are also possible. In particular, the following embodiments are preferred.

First, involving more bins, e.g. at least 5 bins, in the shape histogram are preferred to yield an even more detailed look on the bone distribution. Also taking z-slabs instead of single slices may be advantageous.

Second, a multi-class machine learning framework (i.e., training/matching) would be preferable to classify the slices for a desired list of organs. By this, the precision of the estimates of ischium as well as the disc-label approximations set forth above will even be enhanced.

Third, it is also possible to consider other features from a bone distribution (e.g., circularity, inertia) and/or non-intensity based features when localizing the spine.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A method for localizing a spine in one of an image and a computed tomography image, of a human or animal body, the method comprising the following steps:
    a) acquiring a plurality of slice images of at least a part of a human or animal body; and
    b) automatically selecting slice images and/or portions of slice images from the acquired plurality of slice images by considering at least one parameter characterizing a distribution of bones in the acquired plurality of slice images; wherein
    the selected slice images and/or portions of the slice images include image information about the spine;
    the at least one parameter represents a refined center of gravity of pixels relating to bones within a refinement window in the acquired plurality of slice images, and the refinement window spans around an original center of gravity of pixels relating to the bones in the acquired plurality of slice images; and
    the selected slice images and/or portions of the slice images are selected based on a difference between the original center of gravity and the refined center of gravity.

2. The method according to claim 1, wherein step b) includes truncating image information from the selected slice images and/or portions of the slice images, and the truncated image information is assigned to a region beyond a volume around the spine.

3. The method according to claim 2, wherein the volume around the spine is defined by a rectangular prism.

4. The method according to claim 1, wherein the selected slice images and/or portions of the slice images are displayed by a volume reconstruction.

5. The method according to claim 1, wherein the selected slice images and/or portions of the slice images are analyzed for diagnostic purposes by searching for at least a portion of the spine, including a spinal disc and/or vertebra.

6. An apparatus for localizing a spine in one of an image and a computed tomography image, the image including a plurality of slice images of at least a part of a human or animal body, the apparatus comprising:
    an image processing unit configured and programmed to automatically select slice images and/or portions of slice images from an acquired plurality of slice images by considering at least one parameter characterizing a distribution of bones in the acquired plurality of slice images; wherein
    the selected slice images and/or portions of the slice images include image information about the spine;
    the at least one parameter represents a refined center of gravity of pixels relating to bones within a refinement window in the acquired plurality of slice images, and the refinement window spans around an original center of gravity of pixels relating to the bones in the acquired plurality of slice images; and
    the selected slice images and/or portions of the slice images are selected based on a difference between the original center of gravity and the refined center of gravity.

7. A system for localizing a spine in one of an image and a computed tomography image, of a human or animal body, the system comprising:
    an image acquisition unit including a computed tomography unit, configured and programmed to acquire a plurality of slice images of at least a part of a human or animal body; and
    the apparatus according to claim 6.

8. A method for localizing a spine in one of an image and a computed tomography image, of a human or animal body, the method comprising the following steps:
   a) acquiring a plurality of slice images of at least a part of a human or animal body; and
   b) automatically selecting slice images and/or portions of slice images from the acquired plurality of slice images by considering at least one parameter characterizing a distribution of bones in the acquired plurality of slice images; wherein
   the selected slice images and/or portions of the slice images include image information about the spine; and
   the at least one parameter relates to at least one histogram of pixels relating to bones in a slice image of the acquired plurality of slice images in a left-to-right direction and/or an anterior-posterior direction.

9. The method according to claim 8, wherein slice images showing a histogram of the pixels relating to bones dominant in the left-to-right direction and/or with substantially no contribution in the anterior-posterior direction are truncated.

10. An apparatus for localizing a spine in one of an image and a computed tomography image, the image including a plurality of slice images of at least a part of a human or animal body, the apparatus comprising:
   an image processing unit configured and programmed to automatically select slice images and/or portions of slice images from an acquired plurality of slice images by considering at least one parameter characterizing a distribution of bones in the acquired plurality of slice images; wherein
   the selected slice images and/or portions of the slice images include image information about the spine; and
   the at least one parameter relates to at least one histogram of pixels relating to bones in a slice image of the acquired plurality of slice images in a left-to-right direction and/or an anterior-posterior direction.

11. A system for localizing a spine in one of an image and a computed tomography image, of a human or animal body, the system comprising:
   an image acquisition unit including a computed tomography unit, configured and programmed to acquire a plurality of slice images of at least a part of a human or animal body; and
   the apparatus according to claim 10.

12. A method for localizing a spine in one of an image and a computed tomography image, of a human or animal body, the method comprising the following steps:
   a) acquiring a plurality of slice images of at least a part of a human or animal body; and
   b) automatically selecting slice images and/or portions of slice images from the acquired plurality of slice images by considering at least one parameter characterizing a distribution of bones in the acquired plurality of slice images; wherein
   the selected slice images and/or portions of the slice images include image information about the spine;
   the at least one parameter represents a standard deviation of pixels relating to bones in the acquired plurality of slice images; and
   the acquired plurality of slice images are analyzed by correlating the standard deviation of pixels relating to bones in slice images with a model of a full-body scan.

13. An apparatus for localizing a spine in one of an image and a computed tomography image, the image including a plurality of slice images of at least a part of a human or animal body, the apparatus comprising:
   an image processing unit configured and programmed to automatically select slice images and/or portions of slice images from an acquired plurality of slice images by considering at least one parameter characterizing a distribution of bones in the acquired plurality of slice images; wherein
   the selected slice images and/or portions of the slice images include image information about the spine;
   the at least one parameter represents a standard deviation of pixels relating to bones in the acquired plurality of slice images; and
   the acquired plurality of slice images are analyzed by correlating the standard deviation of pixels relating to bones in slice images with a model of a full-body scan.

14. A system for localizing a spine in one of an image and a computed tomography image, of a human or animal body, the system comprising:
   an image acquisition unit including a computed tomography unit, configured and programmed to acquire a plurality of slice images of at least a part of a human or animal body; and
   the apparatus according to claim 13.

* * * * *